United States Patent [19]

Barreau et al.

[11] Patent Number: 5,025,013

[45] Date of Patent: Jun. 18, 1991

[54] BENZOPYRAN DERIVATIVES, THEIR PREPARATION AND PHARMACEUTICAL COMPOSITIONS CONTAINING THEM

[75] Inventors: Michel Barreau, Montgeron; Jean-Claude Hardy, Cergy Pontoise; Jean-Paul Martin, Colombes; Christian Renault, Taverny, all of France

[73] Assignee: Rhone-Poulenc Sante, Antony, France

[21] Appl. No.: 465,330

[22] Filed: Jan. 16, 1990

[30] Foreign Application Priority Data

Jan. 20, 1989 [FR] France .................................. 89 00657

[51] Int. Cl.$^5$ ................ A61K 31/495; A61K 31/445; C07D 407/06
[52] U.S. Cl. ..................................... 514/253; 514/314; 514/320; 544/360; 544/363; 544/364; 544/373; 544/376; 546/168; 546/174; 546/196; 546/193; 546/194
[58] Field of Search ............... 544/360, 363, 364, 373, 544/376; 546/168, 174, 193, 194, 196; 514/253, 314, 320

[56] References Cited

U.S. PATENT DOCUMENTS 4,563,458  1/1986  Widdig et al. ...................... 514/253

OTHER PUBLICATIONS

Widdig et al., Chem. Abst. 102-6203q (1985).
Froestle, Chem. Abst. 108-167322s (1988).
Hardy et al., Chem. Abst., 111-23390b (1989).

*Primary Examiner*—Cecilia Shen
*Attorney, Agent, or Firm*—Morgan & Finnegan

[57] ABSTRACT

New benzopyran derivatives of general formula (I) in which:

$R_1$ represents a hydrogen or halogen atom or a hydroxy, alkyloxy, nitro, amino, alkylsulphonamido or acylamino radical, R represents (1) radical

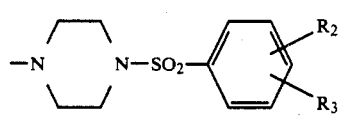

$R_2$ and $R_3$, which may be identical or different, being H, halogen, OH, alkyl, alkyloxy, $NH_2$, alkylsulphonamido or $NO_2$, or (2) a radical

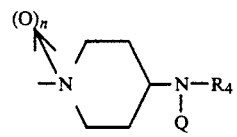

n being 0 or 1, $R_4$ being H, alkyl or optionally substituted phenyl and Q is acyl, alkylsulphonyl or

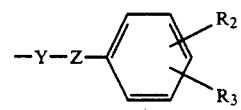

Y being —CO— or —$SO_2$— and Z being a single bond, —$CH_2$— or —NH—, or (3) a radical

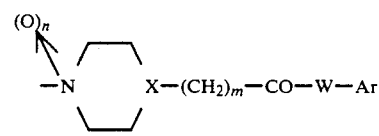

n being 0 or 1, m being 0 or 2, X being C or N (if n=0), W being a bond or —NH— and AR being pyridyl, indolyl, quinolyl, 2-alkylquinolyl or phenyl optionally substituted with $R_2$ and $R_3$, provided that n=0 when X equals N, or (4) a radical of general formula:

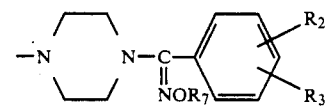

$R_7$ being H or alkyl, or alternatively (5) a radical

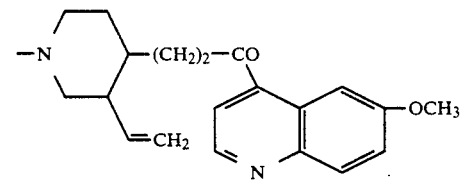

R' and R" are identical and represent hydrogen atoms or alkyl radicals, their isomeric forms and the mixtures thereof, and their addition salts with acids.

These new products are useful as anti-arrhythmic and antifibrillating agents.

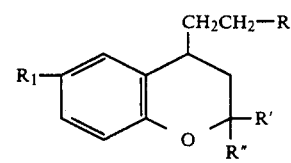

(I)

8 Claims, No Drawings

BENZOPYRAN DERIVATIVES, THEIR PREPARATION AND PHARMACEUTICAL COMPOSITIONS CONTAINING THEM

DETAILED DESCRIPTION OF THE INVENTION

The present invention relates to new benzopyran derivatives of general formula:

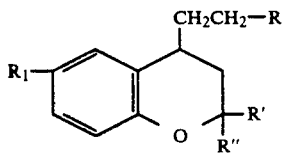  (I)

to their salts, to their preparation and to pharmaceutical compositions containing them.

In German Patent Application No. 3,330,004, a description has been given of 4-(aminomethyl)benzopyran derivatives which are active as hypotensives and muscle relaxants, and corresponding to the formula:

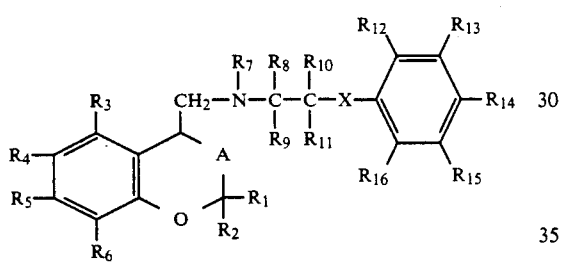

in which

A represents, in particular, a single bond, $R_1$, $R_2$, $R_8$, $R_9$, $R_{10}$ and $R_{11}$ can represent hydrogen atoms, $R_3$, $R_4$, $R_5$ and $R_6$ can be hydrogen atoms or alkyloxy radicals, $R_{12}$ to $R_{16}$ can be inter alia, hydrogen atoms or alkyloxy radicals, or 2 of these adjacent radicals can form a methylenedioxy radical, and $-NR_7-CR_8R_9-CR_{10}R_{11}-X-$ can represent a piperazinyl radical.

It has been found that the products of general formula (I) in which $R_1$ represents a hydrogen or halogen atom or a hydroxy, alkyloxy, nitro, amino, alkylsulphonamido or acylamino radical, R represents 1) a radical of general formula:

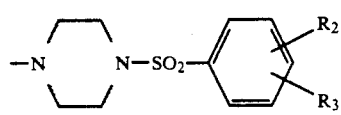  (II)

in which $R_2$ and $R_3$, which may be identical or different, represent hydrogen or halogen atoms or hydroxy, alkyl, alkyloxy, amino, alkylsulphonamido or nitro radicals, or alternatively 2) a radical of general formula:

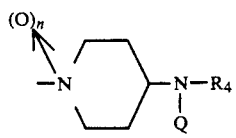  (III)

in which n equals 0 or 1, $R_4$ is a hydrogen atom, an alkyl radical or a radical of structure:

  (IVa)

in which $R_5$ and $R_6$ are hydrogen or halogen atoms or an alkyloxy radical, and Q represents an acyl or alkylsulphonyl radical or a radical of structure:

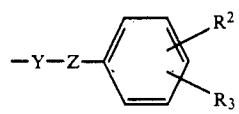  (IVb)

in which $R_2$ and $R_3$ are defined as above, Y represents a carbonyl or sulphonyl radical and Z represents a single bond or a methylene or imino radical, or alternatively 3) a radical of general formula:

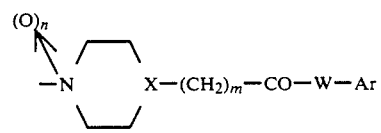  (V)

in which n equals 0 or 1, m equals 0 to 2, X is a carbon atom or X can be a nitrogen atom if $n=0$, W represents a single bond or an imino radical and Ar represents a pyridyl, indolyl, quinolyl or 2-alkylquinolyl radical or Ar represents a phenyl radical optionally substituted with radicals $R_2$ and $R_3$ as defined above, provided that m is other than 0 when X is a nitrogen atom, or alternatively 4) a radical of general formula:

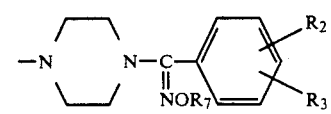  (VI)

in which $R_2$ and $R_3$ are defined as above and $R_7$ denotes a hydrogen atom or an alkyl radical, or alternatively 5) a radical of formula:

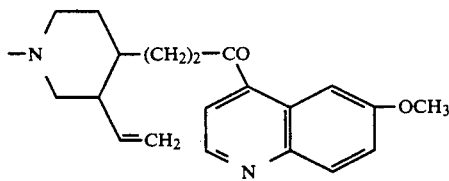

and R' and R", which are identical, represent hydrogen atoms or alkyl radicals,
as well as their salts, bring about an especially advantageous increase in the refractory periods, which corresponds to the antifibrillating effects of class III antiarrhythmic products according to VAUGHAN WILLIAMS's classification.

In the general formula (I), when $R_1$ and/or $R_2$, $R_3$, $R_5$ or $R_6$ (in the symbol R) represent a halogen atom, the letter may be selected from fluorine, chlorine, bromine or iodine. Furthermore, it is understood that the alkyl or acyl radicals and portions may be linear or branched and they contain 1 to 4 carbon atoms.

It is also understood that the products of general formula (I) possess isometric forms, and that these isomers and the mixtures thereof fall within the scope of the present invention.

According to the invention, the products of general formula (I) may be obtained by the action of a product of general formula:

H—R  (VIII)

or its salt, in which R is defined as above provided that n=0, on a benzopyran derivative of general formula:

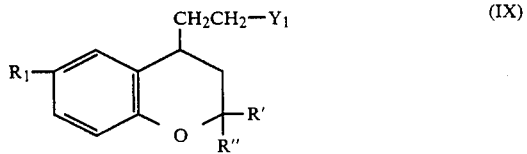

in which $R_1$, R' and R" are defined as above and $Y_1$ represents a halogen atom or an alkylsulphonyloxy or arylsulphonyloxy radical, optionally followed by oxidation of the product obtained when it is desired to prepare a product for which n=1, or alternatively by conversion to oxime when it is desired to obtain a product for which R is a radical defined above at 4) and when the corresponding ketone for which R is a radical defined above at 3), m being equal to 0 and —W—Ar being an optionally substituted phenyl radical, has been obtained.

It is advantageous to work in the presence of an acid-accepting agent. It is also possible to work without an acid-acceptor, in the presence of 2 equivalents of the product of general formula (VIII).

When $Y_1$ represents a halogen atom, it may be selected from chlorine and bromine atoms.

When $Y_1$ represents an alkylsulphonyloxy radical, it represents, in particular, a methylsulphonyloxy radical, and when it represents an arylsulphonyloxy radical, it can be, inter alia, a p-toluenesulphonyloxy radical.

By way of acid-acceptor, an alkali metal hydroxide or alkaline earth metal hydroxide (e.g. sodium hydroxide or potassium hydroxide), an alkali metal carbonate (e.g. sodium bicarbonate, potassium carbonate) or a nitrogenous organic base such as, e.g. triethylamine, is advantageously used.

The reaction is performed in an inert solvent such as a ketone (e.g. acetone, butanone), an ether (e.g. tetrahydrofuran or dioxane), an alcohol (e.g. methanol or ethanol), a hydrocarbon (e.g. hexane or toluene), acetonitrile, dimethylformamide or dimethyl sulphoxide, or in a mixture of such solvents, at a temperature between 20° C. and the refluxing temperature of the reaction mixture.

It is understood that, in cases where $R_1$, $R_2$ and/or $R_3$ (in R) represent an amino radical, the latter is protected beforehand. Similarly, when $R_2$ and/or $R_3$ represent a hydroxy radical, it is preferable to protect this radical prior to the reaction.

The protection is accomplished with any compatible group whose use and removal do not adversely effect the remainder of the molecule. It is performed, in particular, according to the methods described by T. W. Greene, Protective Groups in Organic Synthesis, A. Wiley - Interscience Publication (1981), or by McOmie, Protective Groups in Organic Chemistry, Plenum Press (1973).

Where appropriate, the oxidation is performed by any known method which does not adversely effect the remainder of the molecule. The reaction is accomplished, in particular, by means of an oxidizing agent such as an organic peracid, e.g. peracetic acid or monoperphthalic acid, in an organic solvent such as an ether (e.g. ethyl ether, tetrahydrofuran) or a chlorinated solvent (e.g. chloroform, dichloromethane), at a temperature of between 0° and 25° C. The oxidation may also be accomplished by means of hydrogen peroxide, working in an aqueous medium or in acetic acid or acetic anhydride at a temperature of between −50° and +25° C.

It is understood that, in the case where the molecule bears amino substituents, the oxidation is performed before the liberation of the protective radicals.

Where appropriate, the conversion to a product for which R is a radical of general formula (VI) in which $R_7$ is a hydrogen atom or an alkyl radical is performed by the action of hydroxylamine hydrochloride or O-alkylhydroxyamine.

The reaction is generally performed in the presence of a base (e.g. sodium hydroxide), in an alcohol (absolute ethanol), at a temperature of between 20° and 80° C.

According to the invention, the products of general formula (I) for which the radicals $R_1$, $R_2$ and/or $R_3$ represent a hydroxy radical may also be obtained from the corresponding product of general formula (I) for which the radical $R_1$, $R_2$ and/or $R_3$ to be converted represents an alkyloxy radical, by treatment in a concentrated acid medium.

The reaction is generally performed by treatment with hydrobromic acid, or a mixture of acids, e.g. by treatment with a hydrobromic acid/acetic acid mixture, at the refluxing temperature of the reaction mixture.

According to the invention, the products of general formula (I) for which R is defined as above at 1) and 2) and the symbols $R_1$, $R_2$ and/or $R_3$ represent an amino or alkylsulphonamido radical, or for which $R_1$ represents an acylamino radical, may also be obtained by catalytic hydrogenation in an acid medium of the corresponding benzopyran derivative of general formula (I) for which the radical $R_1$, $R_2$, and/or $R_3$ to be converted represents a nitro radical, and then, when it is desired to obtain a product of general formula (I) for which $R_1$, $R_2$ and/or $R_3$ represent an alkylsulphonamido radical, or for which $R_1$ is an acylamino radical, the amino derivative obtained is converted by sulphonylation or by acylation, respectively.

The hydrogenation is advantageously performed at a temperature of between 20° and 50° C., in an acid such as, e.g., acetic acid or hydrochloric acid, in an organic solvent such as an alcohol (e.g. methanol, ethanol, isopropanol), in a mixture of solvents or in an aqueous-organic medium (e.g. alcohol/water). It is also possible to work directly in the acid without the further addition of a solvent.

By way of a catalyst, palladium, platinum oxide or Raney nickel is generally used.

The reaction is optionally performed under pressure.

The sulphonylation or acylation is accomplished, respectively, by the action of an activated form of an acid alkSO$_3$H or alk'COOH (alk and alk' being alkyl radicals), in particular the acid halide (e.g. acid chloride) or anhydride, and the reaction is carried out in the presence of an acid-acceptor, e.g. a nitrogenous organic base such as a trialkylamine (e.g. triethylamine) or such as pyridine, in an inert organic solvent such as a chlorinated solvent (e.g. dichloromethane, chloroform) or an ether (e.g. ethyl ether, tetrahydrofuran), or in a mixture of these solvents, at a temperature of between −70° and +40° C.

The reaction is optionally performed under nitrogen.

According to the invention, the products of general formula (I) for which R is defined as above at 1) and 3) when X is a nitrogen atom may also be prepared by the action of a halide of structure:

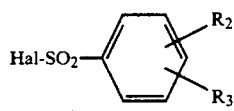

(Xa)

or

Hal—(CH$_2$)$_m$—CO—W—Ar (Xb)

in which $R_2$, $R_3$, W, Ar and m are defined as above and Hal is a halogen atom selected from chlorine or bromine, on a benzopyran derivative of general formula:

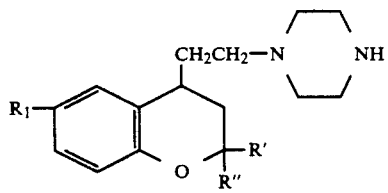

(XI)

in which $R_1$, R' and R'' are defined as above.

It is understood that, when $R_1$, $R_2$ and/or $R_3$ denote amino or hydroxy radicals, the latter are protected prior to the reaction.

The protection and removal of the protective radicals are performed under the conditions described above for the process which consists in reacting the products of general formula (VIII) and (IX).

When a product of general formula (Xa) or (Xb) in which m=0 is reacted, the reaction is performed either in an organic medium, optionally in the presence of an acid-acceptor such as a nitrogenous organic base (e.g. a trialkylamine or a pyridine), in the solvent as mentioned above or a mixture of these solvents, at a temperature of between 0° and 20° C., or in an aqueous-organic medium in the presence of an alkaline condensing agent such as an alkali metal carbonate or bicarbonate or alkaline earth metal carbonate or bicarbonate, at a temperature of between 5° and 20° C.

When a product of general formula (Xb) for which m is 1 or 2 is reacted, the reaction is performed under the conditions described above for preparing a product of general formula (I) from the products of general formulae (VIII) and (IX).

The products of general formula (VIII) may be prepared:

when R is defined as above 1) or 3), X being a nitrogen atom: by the action of a halogenated derivative of formula (Xa) or (IXb) on piperazine under the conditions described above for the reaction of the products of general formula (VIII) with a benzopyran derivative of general formula (IX) in the presence of an excess of piperazine, without the further addition of an acid-acceptor;

when R is defined as at 2): according to the method described in French Patent M 2430, or according to the methods mentioned by Anwer Basha, Tet. Lett., 29(21), 2525 (1988);

when R is defined as at 3), X being a nitrogen atom and W an imino radical: from a benzylpiperazine, by application of the methods mentioned by Anwer Basha, Tet. Lett., 29(21), 2525 (1988) followed by removal of the radical protecting the piperazine;

when R is defined as at 3), X being a carbon atom, a) if a W is a bond: by a Friedel-Crafts reaction between an acid chloride of general formula:

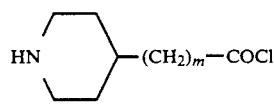

(XII)

in which m equals 1 or 2, and the product of general formula:

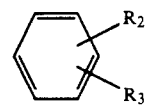

(XIII)

in which $R_2$ and $R_3$ are identical or different and represent hydrogen or halogen atoms or an amino radical protected beforehand, or by application of the method described by P. Rabbe, Ber., 55, 532 (1922);

b) if W is an imino radical: by application of the method described by L. D. Wise et al., J. Med. Chem., 28, 606 (1985);

when R is defined as at 5): according to the method described by A. Quevauviller et al., Ann. Pharm. Franc., 24, 39 (1966).

The products of general formula (IX) may be obtained by the action of a halogenating agent or an activated form of an alkylsulphonic or arylsulphonic acid or a 4-(hydroxyalkyl)benzopyran of general formula

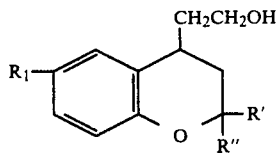

in which $R_1$, $R'$ and $R''$ are defined as above.

When it is desired to prepare a product of general formula (IX) for which $Y_1$ is a halogen atom, the halogenating agents may be selected from thionyl chloride or halogenated phosphorus derivatives such as phosphorus oxychloride or phosphorus tribromide. It is also possible to react allyl bromide in the presence of N,N'-carbonyldiimidazole.

When it is desired to prepare a product of general formula (IX) in which $Y_1$ is alkylsulphonyloxy or arylsulphonyloxy, the anhydride or halide of the corresponding acid is advantageously reacted.

The reaction is generally performed in the presence of a nitrogenous organic base such as triethylamine or pyridine, in an organic solvent such as a chlorinated solvent (e.g. methylene chloride) or an ether (e.g. tetrahydrofuran, dioxane), working at a temperature between 0° C. and the refluxing temperature of the reaction mixture.

The products of general formula (IX) in which $R_1$ is a nitro radical may be obtained by nitration of a derivative of general formula (IX) in which $R_1$ is a hydrogen atom.

It is advantageous to work using a nitric acid/acetic acid mixture at a temperature of between 0° and 20° C.

The products of general formula (IX) in which $R_1$ is a hydroxy radical may also be obtained from a product of general formula (IX) in which $R_1$ is an alkyloxy radical, by treatment in a concentrated acid medium. The reaction is performed under the conditions described above for the production of a product of general formula (I) for which $R_1$ represents a hydroxy radical from the corresponding product for which $R_1$ is an alkyloxy radical.

The 4-(hydroxyalkyl)benzopyran derivative of general formula (XIV) may be prepared by reduction of the corresponding ester of general formula:

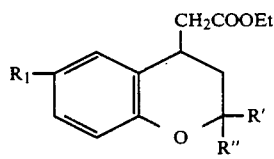

in which $R_1$, $R'$ and $R''$ are defined as above.

The reaction is generally performed using lithium aluminum hydride in an organic solvent such as an ether (e.g. tetrahydrofuran) at a temperature of between 0° and 30° C.

The ester of general formula (XVII) may be obtained by reduction of the benzopyran derivative of general formula:

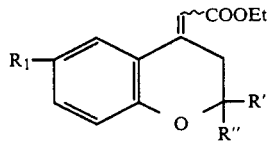

in which $R_1$, $R'$ and $R''$ are defined as above.

The reaction is performed by catalytic hydrogenation in the presence of palladium, in an organic solvent such as an alcohol (e.g. methanol, ethanol), at a temperature of between 10° and 50° C.

The benzopyran derivative of general formula (XVI) may be prepared by a WITTIG reaction, from a 4-chromanone derivative of general formula:

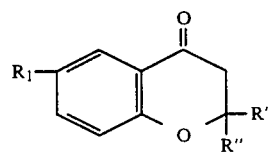

in which $R_1$, $R'$ and $R''$ are defined as above.

The reaction is advantageously performed using ethyl diethylphosphonoacetate in the presence of sodium hydride, in an organic solvent such as an ether (e.g. tetrahydrofuran or dimethoxyethane), at a temperature between 0° C. and the refluxing temperature of the reaction mixture.

The 4-chromanone derivative of general formula (XVII) in which $R_1$ is other than hydrogen may be prepared by application of the method described by PFEIFFER et al., Chem. Ber., 58 (1954), or according to the methods described in G. P. Ellis, Heterocyclic compounds, chromenes, chromanones, and chromones, John Wiley and Sons (1977).

The 4-chromanone derivative of general formula (XVII) in which $R_1$ is a fluorine atom may be prepared according to the method described in French Patent Application 2,588,860.

The 4-chromanone derivatives of general formula (XVII) in which $R_1$ is an amino, alkylsulphonamido or acylamino radical may be obtained from the 4-chromanone derivative of general formula (XVII) for which $R_1$ is a nitro radical, by a procedure similar to the methods described for the preparation of the products of general formula (I) for which radical $R_1$ is defined as above.

2,2-Dimethyl-4-chromanone may be obtained according to the method described in Belgian Patent 844,943.

The products of general formula (Xb) may be prepared:

when W is a bond, by a Friedel-Crafts reaction between an acid chloride of general formula:

$$Hal(CH_2)_mCOCl \qquad (XVIII)$$

in which m is equal to 0 or 1, and a product of general formula (XIII), or when W is an imino radical, according to the method described by L. D. Wise et al., J. Med. Chem., 28, 206 (1985).

The benzopyran derivatives of general formula (XI) may be obtained by the action of piperazine on a benzopyran derivative of general formula (IX).

The reaction is performed under the conditions described above for the reaction of the products of general formula (VIII) with the benzopyran derivatives of general formula (IX), in the presence of an excess of piperazine (2 equivalents), without further addition of an acid-acceptor.

The enantiomers of the products according to the invention may be separated according to known methods.

The procedure is performed, in particular, by preparation of the enantiomer of the hydroxyethylbenzopyran derivative of general formula (XIV), which is converted to a product of general formula (I) according to the process described above.

The optically active derivative of general formula (XIV) is obtained by preparation of an optically active amide of general formula:

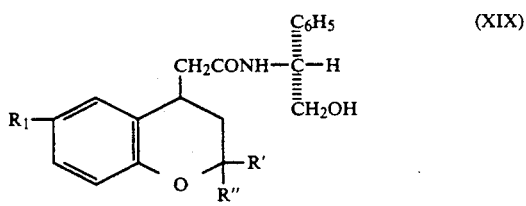

(XIX)

in which $R_1$, $R'$ and $R''$ are defined as above, separation of the isomers by chromatography, hydrolysis of the desired isomer and then reduction of the acid obtained.

The hydrolysis of the isomer of the product of general formula (XIX) may be performed by any known method which does not adversely effect the remainder of the molecule; it is advantageous to work in an acid medium (mixtures of acetic acid and hydrochloric acid) at the refluxing temperature of the reaction mixture.

The reduction of the acid to the alcohol is carried out according to the usual methods. In particular, diborane is used by way of a reducing agent, and it is advantageous to work in an ether such as tetrahydrofuran at temperatures of between 0° and 30° C.

The product of general formula (XIX) may be prepared from the acid of general formula:

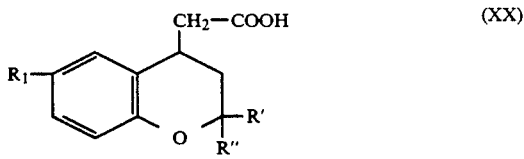

(XX)

in which $R_1$, $R'$ and $R''$ are defined as above, by any known method for preparing an amide from an acid.

The reaction is advantageously performed using the acid chloride of general formula (XX) (which may be prepared in situ), in an inert organic solvent such as a chlorinated solvent (e.g. dichloromethane), in the presence of an acid-acceptor agent such as a nitrogenous organic base (e.g. triethylamine), at a temperature of between 0° and 30° C.

The acid of general formula (XX) may be obtained from the corresponding ester by any known method for obtaining an acid from an ester without affecting the remainder of the molecule.

Saponification of the ester of general formula (XIV) is performed, in particular, with potassium hydroxide in methanol at the refluxing temperature of the reaction mixture.

The acid chloride is prepared by treating the corresponding acid with thionyl chloride at the refluxing temperature of the reaction mixture.

The new benzopyran derivatives according to the invention may be purified, where appropriate, by physical methods such as crystallization or chromatography.

The products according to the invention may be converted to addition salts with acids. The salt formed precipitates after concentration, where appropriate, of the solution, and is separated by filtration, decantation or lyophilization. According to the process of the present invention, the products are generally obtained in the state of an oxalate. These salts may be liberated and converted to salts of other acids according to the usual methods.

As examples of pharmaceutically acceptable salts, there may be mentioned the addition salts with inorganic acids (hydrochlorides, hydrobromides, sulphates, nitrates, phosphates) or organic acids (succinates, fumarates, acetates, propionates, maleates, methanesulphonates, p-toluenesulphonates, isethionates) or substitution derivatives of these compounds.

The products according to the invention exhibit antiarrhythmic properties. In particular, their especially advantageous antifibrillating properties, characteristic of VAUGHAN WILLIAM's class III, result in prolongation of the refractory periods.

They produce, in vitro on guinea pig papillary muscle, an increase of between 5% and values above 30% in the duration of the initial action potential, according to the intracellular action potential recording measurement technique described by E. CORABOEUF and S. WEIDMANN, C. R. Soc. Biol., 143, 1329 (1949).

Moreover, the benzopyran derivatives according to the invention exhibit low toxicity. They have been generally shown to be non-toxic at 300 mg/kg when administered orally to mice.

Of special importance are the products of general formula (I) for which:

$R_1$, $R'$ and $R''$ are hydrogen atoms, and R represents a radical as defined at 1) for which $R_2$ and $R_3$ are hydrogen atoms, or R represents a radical as defined at 2) for which n equals 0, $R_4$ is hydrogen atom, an alkyl radical or a radical of structure (IVa) in which $R_5$ and $R_6$ are hydrogen or halogen atoms or alkyloxy radicals and Q represents an acetyl or methylsulphonyl radical or a radical of general formula (IVb) in which Y is a carbonyl or sulphonyl radical and Z is a bond or a methylene or imino radical, and $R_2$ and $R_3$ are hydrogen or halogen atoms or alkyl or methylsulphonamido radicals, or R represents a radical as defined at 3) for which n equals 0, m equals 0 to 2, W is bond or an imino radical, Ar is pyridyl, indolyl or phenyl optionally substituted with a halogen atom or alkyl or alkyloxy radicals and X is a carbon or nitrogen atom, or R represents a radical as defined at 4) for which $R_7$ represents a hydrogen atom.

And among these more especially active products are the products of general formula (I) given below:

N-{1-[2-(3,4-dihydro-2H-1-benzopyran-4-yl)ethyl]-4-piperidyl}acetanilide and its salts;

1-[2-(3,4-dihydro-2H-1-benzopyran-4-yl)ethyl]-4-nicotinoylpiperazine and its salts;

N-{1-[2-(3,4-dihydro-2H-1-benzopyran-4-yl)ethyl]-4-piperidyl}-N-phenyl-4-fluorobenzamide and its salts;

4-benzoyl-1-[2-(3,4-dihydro-2H-1-benzopyran-4-yl)ethyl]piperidine and its salts; and {1-[2-(3,4-dihydro-2H-1-benzopyran-4-yl)ethyl]-4-piperidyl}phenylmethanoxime and its salts.

The examples which follow, given without implied limitation, illustrate the present invention.

EXAMPLES

In the examples which follow, except where otherwise stated, chromatography is carried out on silica gel (60-200 μ).

EXAMPLE 1

4-(2-Bromoethyl)-3,4-dihydro-2H-benzopyran (1.56 g), N-(4-piperidyl)-3,4-dimethoxyacetanilide (2 g), dry potassium carbonate (1.6 g) and potassium iodide (1.07 g) in 2-butanone (50 cc) are heated to reflux for 6 hours.

The reaction mixture is filtered through sintered glass, then, after evaporation of the solvent under reduced pressure (5.2 kPa), the oil obtained is taken up with potassium carbonate solution (5N) (10 cc) and water (40 cc) is added, and the mixture is then extracted with ethyl acetate (2×75 cc).

The organic phase is then dried over magnesium sulphate and thereafter concentrated to dryness under reduced pressure.

The evaporation residue is chromatographed on a column 2.8 cm in diameter containing silica gel (25 g), eluting with a dichloromethane/isopropanol mixture (90:10 by volume) (210 cc) and collecting 30-cc fractions. The fractions between 60 and 210 cc are concentrated to dryness.

The oil obtained is taken up in the minimum amount of acetone and oxalic acid (0.39 g), dissolved in acetone, is added, the mixture is then concentrated to dryness and the product is crystallized in 2-butanone.

N-{1-[2-(3,4-Dihydro-2H-1-benzopyran-4-yl)ethyl]-4-piperidyl}-3,4-dimethoxyacetanilide acid oxalate (1.6 g) is thereby obtained in the form of a white solid, m.p. 174° C.

N-(4-Piperidyl)-3,4-dimethoxyacetanilide may be prepared by application of the method described in French Patent M 2430, but starting with N-(1-benzyl-4-piperidyl)-3,4-dimethoxyacetanilide (8.4 g), palladium on charcoal (5%) (0.85 g) in an acetic acid/water mixture (70:30 by volume) (100 cc) and performing the hydrogenation at 60° C.

N-(4-Piperidyl)-3,4-dimethoxyacetanilide (6.3 g) is thereby obtained in the form of a whitish powder m.p. 210° C.

N-(1-Benzyl-4-piperidyl)-3,4-dimethoxyacetanilide may be prepared according to the method described in French Patent M 2430, but starting with N-benzyl-4-(3,4-dimethoxyanilino)piperidine (10 g) and acetic anhydride (20 cc) in acetic acid (30 cc).

N-(1-Benzyl-4-piperidyl)-3,4-dimethoxyacetanilide (10.9 g) is thereby obtained in the form of a whitish solid, m.p. 117° C.

N-Benzyl-4-(3,4-dimethoxyanilino)piperidine may be prepared according to the method described in French Patent M 2430, but starting with N-benzylpiperidone (37.8 g) and 3,4-dimethoxyaniline (19.2 g) in toluene (200 cc) with the addition of para-toluenesulphonic acid (0.017 g) and lithium aluminum hydride (1.4 g) in ethyl ether (200 cc).

N-Benzyl-4-(3,4-dimethoxyanilino)piperidine (15 g) is thereby obtained in the form of a whitish solid, m.p. 66° C.

4-(2-Bromoethyl)-3,4-dihydro-2H-benzopyran may be prepared in the following manner:

2-(3,4-Dihydro-2H-1-benzopyran-4-yl)ethanol (13.8 g), then allyl bromide (91.2 g) and finally N, N'-carbonyldiimidazole (12.6 g) are added with stirring to acetonitrile (115 cc).

The mixture is stirred for 3 hours 10 minutes at approximately 20° C. and then 2 hours under reflux.

The reaction mixture is then concentrated under reduced pressure (5.2 kPa) and the residue obtained is chromatographed on a column 5.5 cm in diameter containing silica gel (200 g), eluting with dichloromethane (550 cc) and collecting 100-cc fractions. The fractions between 350 and 550 cc are concentrated to dryness.

4-(2-Bromoethyl)-3,4-dihydro-2H-benzopyran (17.7 g) is thereby obtained in the form of a light brown oil.

Proton NMR spectrum (250 MHz, CDCl$_3$, δ in ppm):
6.8 to 7.2 (m, 4H aromatic),
4.21 (m, —O—CH$_2$—),
3.55 (m, —CH$_2$—Br),
3.08 (m, —CH—),
1.92 and 2.92 (m, —CH$_2$— at the 3-position),
2.08 and 2.34 (m, —CH$_2$CH$_2$Br), 2-(3,4-Dihydro-2H-1-benzopyran-4-yl)ethanol may be prepared in the following manner:

Tetrahydrofuran (500 cc) is added to lithium aluminum hydride (5.96 g) and the mixture is cooled to 0° C. Ethyl 2-(3,4-dihydro-2H-1-benzopyran-4-yl)-ethanoate (17.25 g) in tetrahydrofuran (60 cc) is then added with stirring.

After 1 hour's stirring at 20° C., the mixture is hydrolyzed with stirring by adding hydrated sodium sulphate (10 H$_2$O) until precipitation occurs, and the reaction mixture is then left to stand for 15 hours.

After filtration of the precipitate formed and evaporation of the solvent under reduced pressure, 2-(3,4-dihydro-2H-1-benzopyran-4-yl)ethanol (13.8 g) is isolated in the form of a brown oil.

NMR spectrum (250 MHz, CDCl$_3$, δ in ppm):
6.8 to 7.2 (m, 4H aromatic),
4.22 (m, —O—CH$_2$—),
3.83 (m, —CH$_2$—OH),
3.04 (m, >CH—),
1.83 and 2.90 (m, —CH$_2$— at the 3-position and —CH$_2$—CH$_2$OH),
1.62 (s, —OH).

Ethyl (3,4-dihydro-2H-1-benzopyran-4-yl)ethanoate may be prepared in the following manner:

Ethyl (E,Z)-(3,4-dihydro-2H-1-benzopyran-4-ylidene)acetate (50.6 g) in methanol (1 liter) is hydrogenated at 20° C. at atmosphere pressure in the presence of palladium (5.06 g) on charcoal (10%).

After filtration through kieselguhr and concentration to dryness under reduced pressure (5.2 kPa), ethyl (3,4-dihydro-2H-1-benzopyran-4-yl) ethanoate (48.8 g) is obtained in the form of a pale yellow oil.

NMR spectrum (250 MHz, CDCl$_3$, δ in ppm):
6.75 to 7.2 (m, 4H aromatic),
4.98 (q+m, —O—CH$_2$—+—CO—OCH$_2$—CH$_3$),
3.37 (m, >CH—),
2.53 and 2.82 (dd, —CH$_2$—CO—),
1.87 and 2.18 (m, —CH$_2$— at the 3-position),
1.30 (t, —COO—CH$_2$—CH$_3$), Ethyl (E,Z)-(3,4-dihydro-2H-1-benzopyran-4-ylidene)acetate may be prepared in the following manner:

With stirring, sodium hydride (80%) (20.4 g) is added to anhydrous tetrahydrofuran (1 liter) and ethyl diethylphosphonoacetate (153 g) is then added in small portions while the temperature of the reaction mixture is maintained at around 20° C. The light yellow solution thereby obtained is then treated with 4-chromanone (45 g) in anhydrous tetrahydrofuran (100 cc) while the temperature is maintained below 0° C. After 22 hours at 20° C., the reaction mixture is concentrated under reduced pressure and the oil obtained is then extracted with dichloromethane (2×700 cc). The organic phase is washed with water, then dried over magnesium sulphate and concentrated to dryness under reduced pressure. The evaporation residue is chromatographed on a column 9 cm in diameter containing silica gel (1.6 kg), eluting with a cyclohexane/ethyl acetate mixture (90:10 by volume) (6.3 liters) and collecting 250-cc fractions. Fractions between 2.8 and 6.3 liters are concentrated to dryness.

A mixture (50.6 ) of E and Z isomers of ethyl (3,4-dihydro-2H-1-benzopyran-4-ylidene)acetate is thereby obtained in the form of a pale yellow oil.

NMR spectrum (400 MHz, CDCl$_3$, δ in ppm):
E isomer (75%):
6.8 to 7.61 (m, 4H aromatic),
6.36 (s, =CH—CO—),
4.23 (m, —O—CH$_2$—),
4.23 (m, —CO—OCH$_2$—CH$_3$)
3.41 (m, —CH$_2$— at the 3-position),
1.32 (m, —CO—OCH$_2$—CH$_3$),
Z isomer (25%):
6.8 to 7.83 (m, 4H aromatic),
5.61 (s, =CH—CO—),
4.38 (t, —O—CH$_2$—),
4.23 (m, —CO—OCH$_2$—CH$_3$),
2.65 (t, —CH$_2$— at the 3-position),
1.32 (m, —CO—OCH$_2$—CH$_3$).

EXAMPLE 2

The procedure is as in Example 1, but starting with 4-(2-bromoethyl)-3,4-dihydro-2H-benzopyran (2 g), N-(4-piperidyl)acetanilide (2 g), dry potassium carbonate (2 g) and potassium iodide (1.38 g) in 2-butanone (50 cc).

The oil obtained is taken up with potassium carbonate solution (5N) (10 cc) and water (100 cc) is added, and the mixture is then extracted with ethyl ether (2×75 cc). The combined organic phases are then dried over magnesium sulphate and thereafter concentrated to dryness under reduced pressure (5.2 kPa).

The oil obtained is chromatographed on a column 2.8 cm in diameter containing silica gel (25 g), eluting with dichloromethane/isopropanol mixture (90:10 by volume) and collecting 30-cc fractions. The fractions between 60 and 240 cc are concentrated to dryness.

The oil obtained is dissolved in the minimum amount of acetone at 40° C. and a solution of oxalic acid (0.71 g) in acetone (10 cc) is added.

N-{1-2-(3,4-Dihydro-2H-1-benzopyran-4-yl)ethyl]-4-piperidyl}acetanilide acid oxalate (3.05 g) is thereby obtained in the form of a white solid, m.p. 183° C.

N-(4-Piperidyl)acetanilide may be prepared according to the method described in French Patent M 2430.

EXAMPLE 3

4-(2-Bromoethyl)-3,4-dihydro-2H-benzopyran (1.47 g), 1-(3,4-dimethoxyphenyl)-3-(4-piperidyl)-1-propanone hydrochloride (1.83 g), dry potassium carbonate (1.51 g) and potassium iodide (1 g) in 2-butanone (50 cc) are heated to reflux for 18 hours.

The reaction mixture is filtered through sintered glass and then, after evaporation of the solvent under reduced pressure (5.2 kPa), the reaction mixture is taken up with distilled water (20 cc) and extracted with ethyl acetate (3×70 cc). The organic phase is then dried over magnesium sulphate and thereafter concentrated to dryness under reduced pressure (5.2 kPa).

The residue obtained is purified by chromatography on a column 5.5 cm in diameter containing silica gel (32-63 μ) (200 g), eluting with a dichloromethane/ethanol mixture (95:5 by volume) (1.6 liters) and then a dichloromethane/ethanol mixture (90:10 volume) (4.4 liters) and collecting 200-cc fractions. The fractions between 2.6 and 4.4 liters are concentrated to dryness.

The product obtained is dissolved in the minimum amount of acetone at 40° C. and a solution of oxalic acid (0.6 g) in acetone is added. The white precipitate formed is filtered off on sintered glass and then recrystallized a first time in ethanol (250 cc) and a second time in a mixture (100 cc) of ethanol and 2-butanone (75:25 by volume).

3-{1-[2-(3,4-dihydro-2H-1-benzopyran-4-yl)ethyl]-4-piperidyl}-1-(3,4-dimethoxyphenyl)propanone acid oxalate (2.65 g) is thereby obtained in the form of a white solid, m.p. 175° C.

1-(3,4-Dimethoxyphenyl)-3-(4-piperidyl)-1-propanone may be prepared in the following manner:

Aluminum chloride (47 g) is added gradually in portions (5-6 g) to a solution of 1,2-dimethoxybenzene (140 cc) in dichloromethane (200 cc) and 1-benzoyl-4-piperidylpropionic acid chloride (75 g).

The reaction mixture is then heated for 9 hours to boiling and thereafter left overnight at room temperature. The reaction mixture is then poured into ice and, after settling has taken place and washes with distilled water, the organic phase is concentrated to dryness.

The oil obtained is taken up with 3N sodium hydroxide solution (200 cc) and the mixture is extracted with ethyl acetate. The organic phase is separated and then, after washes with distilled water, is concentrated to dryness and the oil obtained is brought to reflux for 48 hours in 3.25N hydrochloric acid solution (1.2 liters).

After cooling, the benzoic acid crystals are filtered off and the filtrate is alkalinized with concentrated sodium hydroxide solution. After three extractions with dichloromethane, the organic phase is washed with water and then dried over magnesium sulphate. It is concentrated to dryness and the oil obtained is taken up with a 4N solution of hydrochloric acid in ethanol.

1-(3,4-Dimethoxyphenyl)-3-(4-piperidyl)propanone hydrochloride (8.49 g) is thereby obtained in the form of white crystals, m.p. 193° C.

1-Benzoyl-4-piperidylpropionic acid chloride may be prepared in the following manner:

1-Benzoyl-4-piperidylpropionic acid (75.4 g) is heated to reflux for 2 hours with thionyl chloride (84 cc) in chloroform (400 cc). After concentration to dryness under reduced pressure 1-benzoyl-4-piperidylpropionic acid chloride (75 g) is obtained in the form of a brown solid, which is used without further treatment for the next step.

1-Benzoyl-4-piperidylpropionic acid may be prepared according to the methods described in Beil., 22 (III/IV), 161 and by C. F. Koelschr, J. Am. Chem. Soc., 65, 2460 (1943).

EXAMPLE 4

The procedure is as in Example 3, but starting with 4-(2-bromoethyl)-3,4-dihydro-2H-benzopyran (1.60 g), N-(4-fluorophenyl)-N-(4-piperidyl)-4-fluorobenzamide hydrochloride (2.30 g), dry potassium carbonate (1.80 g) and potassium iodide (0.80 g) in 2-butanone (50 cc).

After 18 hours under reflux, the reaction mixture is filtered through sintered glass and then, after evaporation of the solvent under reduced pressure (5.2 kPa), the yellow oil obtained is taken up with dichloromethane (100 cc) and washed with 20% strength ammonia solution. After washing with water, the organic phase is then dried over magnesium sulphate and thereafter concentrated to dryness under reduced pressure (5.2 kPa). The yellow oil obtained is purified by chromatography on a column 5.5 cm in diameter containing silica gel (63–200 μ) (100 g), eluting with a dichloromethane/ethanol mixture (95:5 by volume) (810 cc) and collecting 30-cc fractions. The fractions between 200 and 810 cc are concentrated to dryness.

The yellow oil obtained is taken up in the minimum amount of acetone and oxalic acid (0.90 g), dissolved in acetone, is added. The white precipitate formed is filtered off on sintered glass and is then recrystallized in ethanol (50 cc).

N-{1-[2-(3,4-Dihydro-2H-1-benzopyran-4-yl)ethyl]-4-piperidyl}-N-(4-fluorophenyl)-4-fluorobenzamide acid oxalate (2 g) is thereby obtained in the form of a white powder, m.p. 150° C.

N-(4-Fluorophenyl)-N-(4-piperidyl)-4-fluorobenzamide hydrochloride may be prepared in the following manner:

N-(1-Benzyl-4-piperidyl)-N-(4-fluorophenyl)-4-fluorobenzamide hydrochloride (3.2 g) in 95% strength ethanol (50 cc) is hydrogenated at 60° C. at atmospheric pressure in the presence of palladium hydroxide (0.5 g). After filtration through kieselguhr and concentration to dryness under reduced pressure (5.2 kPa), N-(4-fluorophenyl)-N-(4-piperidyl)-4-fluorobenzamide hydrochloride (2.3 g) is obtained in the form of a white powder, m.p. 170° C.

N-(1-Benzyl-4-piperidyl)-N-(4-fluorophenyl)-4-fluorobenzamide hydrochloride may be prepared in the following manner:

N-Benzyl-4-(4-fluoroanilino)piperidine (2.8 g), dissolved in trichloromethane (30 cc), is stirred for 18 hours with 4-fluorobenzoic acid chloride (2 cc) and in the presence of triethylamine (5 cc). The reaction mixture is then washed twice with sodium hydroxide solution (3N) (30 cc) thereafter with water (30 cc). The organic phase is then dried over magnesium sulphate and thereafter concentrated under reduced pressure (5.2 kPa). By the addition of a 3.4N solution (5 cc) of hydrochloric acid in isopropanol and recrystallization in acetone/ethanol mixture (50:50 by volume) (100 cc), N-(1-benzyl-4-piperidyl)-N-(4-fluorophenyl)-4-fluorobenzamide hydrochloride (3.2 g) is obtained in the form of a white powder, m.p. 210° C.

N-Benzyl-4-(4-fluoroanilino)piperidine may be prepared in the following manner:

Benzylpiperidone (2 g), dissolved in toluene (10 cc), is stirred under argon for 48 hours at room temperature in the presence of 4-fluoroaniline (1.4 g) and 5 Å molecular sieve (4 g). After filtration and concentration to dryness under reduced pressure (5.2 kPa), yellow crystals are obtained, which are then dissolved in methanol (30 cc). This solution is then added to a solution, cooled to 0°–5° C., of sodium cyanoborohydride (1.34 g) and zinc chloride (1.4 g) in methanol (20 cc). After 20 hours at room temperature, the product is taken up with 10N sodium hydroxide solution (5 cc) and with water (20 cc) and the mixture is heated to reflux for 1 hour. The mixture is filtered through a sinter and the filtrate is extracted twice with dichloromethane (100 cc). The organic phase is then dried over magnesium sulphate and thereafter concentrated to dryness under reduced pressure (5.2 kPa). N-Benzyl-4-(4-fluoroanilino)piperidine (2.8 g) is thereby obtained in the form of a whitish powder, m.p. 84° C.

EXAMPLE 5

The procedure is as in Example 4, but starting with 4-(2-bromoethyl)-3,4-dihydro-2H-benzopyran (1.6 g), N-phenyl-N-(4-piperidyl)-4-fluorobenzamide hydrochloride (2.21 g), dry potassium carbonate (1.8 g) and potassium iodide (0.8 g) in 2-butanone (50 cc). The oil obtained is taken up in the minimum amount of acetone and oxalic acid (0.6 g), dissolved in acetone, is added. The white precipitate formed is filtered off on sintered glass and then recrystallized in ethanol (50 cc). N-{1-[2-(3,4-Dihydro-2H-1-benzopyran-4-yl)ethyl]-4-piperidyl}-N-phenyl-4-fluorobenzamide acid oxalate (2.7 g) is thereby obtained in the form of a white solid, m.p. 161° C.

N-Phenyl-N-(4-piperidyl)-4-fluorobenzamide hydrochloride is prepared as described in Example 4 for N-(4-fluorophenyl)-N-(4-piperidyl)-4-fluorobenzamide.

EXAMPLE 6

The procedure is as in Example 4, but starting with 4-(2-bromoethyl)-3,4-dihydro-2H-benzopyran (1.6 g), N-phenyl-N-(4-piperidyl)benzamide hydrochloride (2.1 g), dry potassium carbonate (1.8 g) and potassium iodide (0.8 g) in 2-butanone (50 cc). The oil obtained is taken up in the minimum amount of acetone and oxalic acid (0.6 g), dissolved in acetone, is added. The white precipitate formed is filtered off on sintered glass and then recrystallized in ethanol (45 cc).

N-{1-[2-(3,4-Dihydro-2H-1-benzopyran-4-yl)ethyl]-4-piperidyl}-N-phenylbenzamide acid oxalate (2.7 g) is thereby obtained in the form of a white solid, m.p. 135° C.

N-Phenyl-N-(4-piperidyl)benzamide hydrochloride is prepared as described in Example 4 for N-(4-fluorophenyl)-N-(4-piperidyl)-4-fluorobenzamide.

EXAMPLE 7

The procedure is as in Example 1, but starting with 4(2-bromoethyl)-3,4-dihydro-2H-benzopyran (2.5 g), N-(2,6-dimethylphenyl)-N-(4-piperidyl)-4-fluorobenzamide (3.26 g), dry potassium carbonate (2.76 g) and potassium iodide (1.66 g) in 2-butanone (25 cc), heating for 3 hours.

The 2-butanone is evaporated off under reduced pressure (5.2 kPa) and the residue is taken up in water (50 cc) and extracted with dichloromethane (100 cc, 2×50 cc). The combined organic phases are dried over magnesium sulphate and then concentrated to dryness under reduced pressure (5.2 kPa). The oil obtained is chromatographed on a column 4 cm in diameter containing silica gel (150 g), eluting with a dichloromethane/ethanol mixture (98:2 by volume) and collecting 25-cc fractions. The fractions between 125 and 11100 cc are concentrated to dryness. The oil obtained is dissolved in absolute ethanol (45 cc) and treated with oxalic acid (0.83 g) in the heated state. The product is left to crystallize at ±5° C.

N-{1-[2-(3,4-Dihydro-2H-1-benzopyran-4-yl)ethyl]-4-piperidyl}-N-(2,6-dimethylphenyl)-4-fluorobenzamide acid oxalate (3.75 g) is thereby obtained in the form of a white solid, m.p. 205° C.

N-(2,6-Dimethylphenyl)-N-(4-piperidyl)-4-fluorobenzamide may be prepared in the following manner:

A solution of N-(1-benzyl-4-piperidyl)-N-(2,6-dimethylphenyl)-4-fluorobenzamide (8.57 g) in ethanol (100 cc) is treated with 12N aqueous hydrochloric acid solution (2 cc) and palladium (1 g) on charcoal (10% palladium). This suspension is subjected to the action of hydrogen at atmospheric pressure at 55° C. After 4 hours, the theoretical volume has been absorbed, the mixture is cooled and the catalyst is filtered off and washed with ethanol (3×20 cc).

The ethanol is evaporated off under reduced pressure (5.2 kPa). The solid obtained is taken up in water (50 cc), treated with 10N sodium hydroxide (2.5 cc) and extracted with dichloromethane (7×50 cc). The combined organic phases are concentrated to dryness under reduced pressure (5.2 kPa).

N-(2,6-Dimethylphenyl)-N-(4-piperidyl)-4-fluorobenzamide (6.6 g) is obtained in the form of a brown oil.

NMR spectrum (300 MHz, CDCl$_3$, δ in ppm, J in Hz)
6.65 to 7.3 (m, 7H aromatic),
4.1 (m, 1H, piperidine >N—CH<)
3.06 (broad d, J=12.5, 2H, equatorial of piperidine >N—CH$_2$— groups),
2.65 (broad t, J=12.5+s, 3H, axial of piperidine >N—CH$_2$— groups+—NH—),
2.17 (s, 6H: Ar—CH$_3$)
1.88 (broad d, J=12.5, 2H; equatorial H of piperidine —CH$_2$— groups),
1.66 (m, 2H: axial H of piperidine —CH$_2$— groups).

N-(2,6-Dimethylphenyl)-N-(1-benzyl-4-piperidyl)-4-fluorobenzamide may be prepared in the following manner:

Triethylamine (4.5 cc) and then 4-fluorobenzoic acid chloride (3.1 cc) are added to a solution of N-(2,6-dimethylphenyl)-N-(1-benzyl-4-piperidyl)amine (6.5 g) in trichloromethane (100 cc) while the temperature is maintained at ±25° C. After 30 minutes, water (100 cc) is poured in, and then after 16 hours, settling is allowed to take place and the aqueous phase is re-extracted with trichloromethane (2×50 cc). The combined organic phases are dried over magnesium sulphate and then concentrated to dryness under reduced pressure (5.2 kPa).

The oil obtained is chromatographed on a column 6 cm in diameter containing silica gel (500 g), eluting first with a dichloromethane/ethanol mixture (98:2 by volume) (2750 cc) and then with the same solvent mixture (95:5 by volume). 125-cc fractions are collected. The fractions between 3500 and 4500 cc are concentrated to dryness. N-(1-Benzyl-4-piperidyl)-N-(2,6-dimethylphenyl)-4-fluorobenzamide (8.7 g) is obtained in the form of a brown resin.

NMR spectrum (300 MHz, DMSO-d$_6$, δ in ppm, J in Hz)
6.95 to 7.4 (m, 12H aromatic),
3.9 (m, 1H, piperidine >CH—N<),
3.47 (s, 2H, exo >—CH$_2$—),
2.86 (broad d, J=12.5, 2H,: equatorial H of piperidine >N—CH$_2$— groups),
2.23 (s, 6H, Ar—CH$_3$),
2.03 (dt, J=12.5 and 3, 2H: axial H of piperidine >N—CH$_2$— groups),
1.7 to 1.9 (m, 4H, piperidine —CH$_2$—).

N-(2,6-Dimethylphenyl)-N-(1-benzyl-4-piperidyl)amine may be prepared in the following manner:

2,6-Dimethylaniline (14.8 cc) is added during 2 hours to a solution of N-benzyl-4-piperidone (18.9 g) in toluene (100 cc), collecting the water formed using a Dean and Stark apparatus. The toluene is evaporated off under reduced pressure (5.2 kPa).

The oil obtained is dissolved in methanol (100 cc) and added to a mixture of sodium cyanoborohydride (12.65 g) and zinc chloride (13.6 g) in methanol (150 cc), at a temperature below 20° C. After 2 hours at 20° C., 10N sodium hydroxide solution (50 cc) is poured in, water (100 cc) is added and the mixture is heated to reflux for 30 minutes. It is cooled to room temperature for 16 hours and dichloromethane (200 cc) is added. The aqueous phase is separated after settling has taken place and re-extracted with dichloromethane (2×100 cc). The organic phases are combined and dried over magnesium sulphate, and then concentrated to dryness (5.2 kPa). The oil obtained is chromatographed on a column 7 cm in diameter containing silica gel (900 g), eluting first with pure dichloromethane (2500 cc) and then with a dichloromethane/ethanol mixture (97:3 by volume) and collecting 250-cc fractions. The combined fractions between 7250 cc and 10,500 cc are concentrated to dryness to give N-(2,6-dimethylphenyl)-N-(1-benzyl-4-piperidyl)amine (6.5 g) in the form of a brown oil.

NMR spectrum (250 MHz, CDCl$_3$, δ in ppm and J in Hz)
6.75 to 7.45 (m, 8H aromatic),
3.54 (s, 2H, exo >N—CH$_2$—),
3.02 (m, 1H, piperidine >N—CH<),
2.92 (broad d, J=12.5, 2H: equatorial H of piperidine >N—CH$_2$— groups),
2.77 (cx, 1H, —NH—),
2.3 (s, 6H, Ar—CH$_3$),
2.03 (dt, J=12.5 and 2, 2H: axial H of piperidine >N—CH$_2$— groups)
1.93 (broad d, J=12.5, 2H: equatorial H of piperidine —CH$_2$— groups),
1.5 (m, 2H: axial H of piperidine —CH$_2$— groups).

EXAMPLE 8

The procedure is as in Example 4, but starting with 4-(2-bromoethyl)-3,4-dihydro-2H-benzopyran (1.6 g), N-(4-chlorophenyl)-N-(4-piperidyl)-4-methanesulphonamidobenzamide hydrochloride (2.95 g), dry potassium carbonate (0.9 g) and potassium iodide (0.8 g) in 2-butanone (50 cc). The residue obtained is taken up with ethanol (100 cc) and 1N hydrochloric acid solution (6.6 cc) and then concentrated until crystallization begins. The white precipitate formed is filtered off on sintered glass and is then recrystallized in methanol (100 cc).

N-{1-{2-(3,4-Dihydro-2H-1-benzopyran-4-yl)ethyl]-4-piperidyl-N-(4-chlorophenyl)-4-methanesulphonamidobenzamide hydrochloride (2.1 g), m.p. approximately 260° C. is thereby obtained.

EXAMPLE 9

The procedure is as in Example 4, but starting with 4-(2-bromoethyl)-3,4-dihydro-2H-benzopyran (1.6 g), N-(4-chlorophenyl)-N-(4-piperidyl)-phenylacetamide hydrochloride (2.42 g), dry potassium carbonate (1.80 g) and potassium iodide (0.80 g) in 2-butanone (50 cc).

The oil obtained is taken up in the minimum amount of acetone and oxalic acid (0.6 g), dissolved in acetone, is added. The white precipitate formed is filtered off on sintered glass and then recrystallized in ethanol (50 cc).

N-{1-[2-(3,4-Dihydro-2H-1-benzopyran-4-yl)ethyl]-4-piperidyl}-N-(4-chlorophenyl)phenylacetamide acid oxalate (2.3 g) is thereby obtained in the form of a white solid, m.p. 185° C.

N-(4-Chlorophenyl)-N-(4-piperidyl)phenylacetamide hydrochloride has been prepared in a similar manner to N-(3-chlorophenyl)-N-(4-piperidyl)phenylacetamide, Chem. Abstr., 93 132380.

EXAMPLE 10

The procedure is as in Example 1, but starting with 4-(2-bromoethyl)-3,4-dihydro-2H-benzopyran (1.94 g), N-isopropyl-N-(4-piperidyl)-4-fluorobenzamide (2.21 g), dry potassium carbonate (3.05 g) and potassium iodide (1.22 g) in 2-butanone (20 cc), stirring for 4 hours 30 minutes. The butanone is evaporated off under reduced pressure (5.2 kPa) and the residue is taken up in water (50 cc), which is extracted with dichloromethane (50 cc, then 2×25 cc). The combined organic phases are dried over dry magnesium sulphate and then concentrated to dryness under reduced pressure (5.2 kPa). The oil obtained is chromatographed on a column 3 cm in diameter containing silica gel (100 g), eluting with a dichloromethane/ethanol mixture (95:5 by volume) and collecting 25-cc fractions. The fractions between 150 and 950 cc are concentrated to dryness. The oil obtained is dissolved in ethyl acetate (30 cc) and treated with a 5N solution (1.5 cc) of hydrochloric acid in isopropanol.

N-{1-[2-(3,4-Dihydro-2H-1-benzopyran-4-yl)ethyl]-4-piperidyl}-N-isopropyl-4-fluorobenzamide hydrochloride (3 g) is thereby obtained in the form of a white solid, m.p. 165° C.

N-Isopropyl-N-(4-piperidyl)-4-fluorobenzamide hydrochloride may be prepared in the following manner:

3N aqueous hydrochloric acid (20 cc) and then palladium (1.5 g) on charcoal (10% palladium) are added to a solution of N-(1-benzyl-4-piperidyl)-N-isopropyl-4-fluorobenzamide (3.35 g) in absolute ethanol (100 cc). This suspension is subjected to the action of hydrogen at atmospheric pressure at a temperature of 55° C. After 4 hours, the theoretical volume has been absorbed. The mixture is cooled and the catalyst is filtered off and washed with ethanol and then with water. The ethanol is evaporated off under reduced pressure (5.2 kPa). The solid obtained is recrystallized in absolute ethanol (20 cc).

N-Isopropyl-N-(4-piperidyl)-4-fluorobenzamide hydrochloride (2.6 g) is thereby obtained in the form of a white solid, m.p. above 260° C.

NMR spectrum (200 MHz, DMSO-d$_6$, $\delta$ in ppm and J in Hz):

1.2 (cx, 6H, isopropyl —CH$_3$), 1.7 (broad d, J=16, 2H: equatorial H of piperidine —CH$_2$— groups), 2.65 to 3.20 (m, 4H: axial H of piperidine —CH$_2$— and >N—CH$_2$— groups), 3.28 (broad d, J=16, equatorial H of piperidine —N—CH$_2$— groups), 3.4 to 3.8 (m, 2H, piperidine >CH—N< and isopropyl >CH—), 7.2 to 7.5 (m, aromatic), N-(1-Benzyl-4-piperidyl)-N-isopropyl-4-fluorobenzamide may be prepared in the following manner:

4-fluorobenzoic acid chloride (3.7 cc) is added to a solution of 1-benzyl-4-isopropylaminopiperidine dihydrochloride hydrate (3.83 g) and triethylamine (15 cc) in trichloromethane (50 cc). After 6 hours' stirring at 20° C., water (50 cc) is poured in and the mixture is left to stand for 16 hours. Settling is allowed to take place and the aqueous phase is extracted with trichloromethane (50 cc). The organic phases are washed with water (50 cc), then dried over magnesium sulphate and concentrated to dryness under reduced pressure (5.2 kPa). The oil obtained is chromatographed on a column 4 cm in diameter containing silica gel (200 g), eluting first with a dichloromethane/ethanol mixture (95:5 by volume) (1400 cc) and collecting 60-cc fractions. The fractions between 480 and 1980 cc are concentrated to dryness to give an ocher solid which is recrystallized in a diisopropylether/ethanol mixture (95:5 by volume) to obtain N-(1-benzyl-4-piperidyl)-N-isopropyl-4-fluorobenzamide (1.2 g) in the form of a white solid, m.p. 98° C.

1-Benzyl-4-isopropylaminopiperidine dihydrochloride may be prepared in the following manner:

Isopropylamine hydrochloride (14.3 g) is added to a solution of N-benzyl-4-piperidone hydrochloride (6.8 g) in ethanol (100 cc) and the mixture is cooled to +10° C. Sodium cyanoborohydride (1.9 g) is then added and the mixture is thereafter stirred for 16 hours at 20° C.

10N sodium hydroxide (50 cc) is poured in and the mixture is stirred for 22 hours at 20° C. The ethanol is evaporated off under reduced pressure (5.2 kPa) and the residual oil extracted with dichloromethane (3×50 cc). The combined organic phases are dried over magnesium sulphate and concentrated to dryness. The residual oil is dissolved in absolute ethanol (50 cc) and treated with a 5N solution (11.5 cc) of hydrochloric acid in isopropanol. 1-Benzyl-4-isopropylaminopiperidine dihydrochloride hydrate (4.24 g) is thereby obtained in the form of a white solid, m.p. above 260° C.

NMR spectrum (200 MHz, DMSO-d$_6$, $\delta$ in ppm and J in Hz):

At room temperature, the mixture of two conformers in proportions 85:15 is observed)

7.30 to 7.80 (m, 5H aromatics), 4.26 and 4.46 (d and limiting ab: 2H in total and in a ratio 85:15 respectively; exo >N—CH$_2$—), 2.80 to 3.50 (m, 6H, piperidine >N—CH$_2$— and >N—CH< and isopropyl >CH—), 1.90 to 2.30 (m, 4H, piperidine —CH$_2$—), 1.28 and 1.32 (2d, J=7, 6H in total and in a ratio 85:15 respectively, isopropyl —CH$_3$).

EXAMPLE 11

The procedure is as in Example 4, but starting with 4-(2-bromoethyl)-3,4-dihydro-2H-benzopyran (1.6 g), 1-phenyl-1-(4-piperidyl)-3-(2,6-dimethylphenyl)urea hydrochloride (2.4 g), dry potassium carbonate (1.8 g) and potassium iodide (0.8 g) in 2-butanone (50 cc).

The solid residue obtained is taken up in the minimum amount of acetone and oxalic acid (0.6 g) dissolved in acetone, is added.

The shite precipitate formed is filtered on sintered glass and is then recrystallized in 95% strength aqueous ethanol (150 cc).

1-{1[2-(3,4-Dihydro-2H-1-benzopyran-4-yl)ethyl]-4-piperidyl}-1-phenyl-3-(2,6-dimethylphenyl)urea acid oxalate (2.1 g) is thereby obtained in the form of a white powder, m.p. 190° C. (decomposition).

1-Phenyl-1-(4-piperidyl)-3-(2,6-dimethylphenyl)-urea hydrochloride is prepared by a procedure similar to the method described in Chem. Abstr. 88, 022640.

EXAMPLE 12

The procedure is as in Example 1, but starting with 4-(2-bromoethyl)-3,4-dihydro-2H-benzopyran (2.65 g), N-(2,6-dimethylphenyl)-4-piperidineacetamide (2.46 g), dry potassium carbonate (2.76 g) and potassium iodide (1.66 g) in dry dimethylformamide (25 cc), heating for 4 hours to 60° C. The dimethylformamide is evaporated off under reduced pressure (1 kPa) and the residue is taken up in water (50 cc) which is extracted with dichloromethane (3×50 cc). The combined organic phases are dried over magnesium sulphate and then concentrated to dryness under reduced pressure (5 kPa). The solid obtained is chromatographed on a column 4 cm in diameter containing silica gel (120 g), eluting with a toluene/diethylamine mixture (95:5 by volume) and collecting 25-cc fractions. The fractions between 175 and 1000 cc are concentrated to dryness. The solid obtained is recrystallized in acetone (20 cc).

1-[2-(3,4-Dihydro-2H-1-benzopyran-4-yl)ethyl]-N-(2,6-dimethylphenyl)-4-piperidineacetamide (2.55 g) is thereby obtained in the form of a white solid, m.p. 136° C.

N-(2,6-Dimethylphenyl)-4-piperidineacetamide is prepared as described in Chem. Abstr., 76, 152718x.

EXAMPLE 13

The procedure is as in Example 1, but starting with 4-(2-bromoethyl)-3,4-dihydro-2H-benzopyran (2.41 g), N-(nicotinoyl)piperazine dihydrochloride (2.64 g), dry potassium carbonate (4.15 g) and potassium iodide (1.66 g) in 2-butanone (25 cc), heating for 3 hours 30 minutes.

The butanone is evaporated off under reduced pressure (5.2 kPa) and the oil obtained is taken up in water (50 cc) which is extracted with dichloromethane (50 cc, then 2×25 cc). The combined organic phases are dried over magnesium sulphate and then concentrated to dryness under reduced pressure (5.2 kPa).

The oil obtained is chromatographed on a column 4 cm in diameter containing silica gel (200 g), eluting with a toluene/diethylamine mixture (95:5 by volume) and collecting 60-cc fractions. The fractions between 1140 and 1500 cc are concentrated to dryness.

The oil obtained is dissolved in absolute ethanol (20 cc) and treated with a 5N solution (2.5 cc) of hydrochloric acid in isopropanol.

1-[2-(3,4-Dihydro-2H-1-benzopyran-4-yl)ethyl]-4-nicotinoylpiperazine dihydrochloride monohydrate (2.35 g) is thereby obtained in the form of white crystals, m.p. 190° C. (decomposition).

N-(Nicotinoyl)piperazine is prepared as described in Chem. Abstr., 42, 6002 g (1948).

EXAMPLE 14

The procedure is as in Example 1, but starting with 4-(2-bromoethyl)-3,4-dihydro-2H-benzopyran (2.9 g), 4-benzoylpiperidine (2.05 g), dry potassium carbonate (3 g) and potassium iodide (1.8 g) in 2-butanone (25 cc), heating for 1 hour 30 minutes. The butanone is evaporated off under reduced pressure (5.2 kPa) and the oil obtained is taken up in water (50 cc) which is extracted with dichloromethane (50 cc, then 2×25 cc). The combined organic phases are dried over magnesium sulphate and then concentrated to dryness under reduced pressure (5.2 kPa). The oil obtained is chromatographed on a column 4 cm in diameter containing silica gel (200 g), eluting with a dichloromethane/ethanol mixture (95:5 by volume) and collecting 60-cc fractions. The fractions between 360 and 1560 cc are concentrated to dryness (5.2 kPa). The oil obtained is dissolved in acetone (40 cc) and treated with a 5N solution (2.2 cc) of hydrochloric acid in isopropanol.

4-Benzoyl-1-[2-(3,4-dihydro-2H-1-benzopyran-4-yl)ethyl]piperidine hydrochloride (2.65 g) is thereby obtained in the form of a white solid, m.p. 210° C. (decomposition).

EXAMPLE 15

The procedure is as in Example 1, but starting with 4-(2-bromoethyl)-3,4-dihydro-2H-benzopyran (2.41 g), 4-(4-fluorobenzoyl)piperidine paratoluenesulphonate (3.8 g), dry potassium carbonate (2.75 g) and potassium iodide (1.66 g) in 2-butanone (25 cc), heating for 2 hours. The butanone is evaporated off under reduced pressure (5.2 kPa) and the oil obtained is taken up in water (50 cc) which is extracted with dichloromethane (50 cc, then 2×25 cc). The combined organic phases are dried over magnesium sulphate and then concentrated to dryness under reduced pressure (5.2 kPa). The solid obtained is dissolved in lukewarm acetone (70 cc) and treated with a 5N solution (2.1 cc) of hydrochloric acid in isopropanol.

1-[2-(3,4-Dihydro-2H-1-benzopyran-4-yl)ethyl]-4-(4-fluorobenzoyl)piperidine hydrochloride (3 g) is thereby obtained in the form of a white solid, m.p. 200° C. (decomposition).

EXAMPLE 16

The procedure is as in Example 4, but starting with 4-(2-bromoethyl)-3,4-dihydro-2H-benzopyran (1.5 g), 3-[(4-piperidyl)carbonyl]indole acid oxalate (2.16 g), dry potassium carbonate (1.71 g) and potassium iodide (1.085 g) in butanone (50 cc). The residue obtained is taken up in the heated state with ethanol (20 cc) and 1N hydrochloric acid solution (6.2 cc) and then concentrated until crystallization begins. The precipitate formed is filtered off on sintered glass and is then recrystallized in 95% strength ethanol (50 cc). 3-[N-{1-[2-(3,4-Dihydro-2H-1-benzopyran-4-yl)ethyl]-4-piperidyl} carbonyl]indole hydrochloride (0.68 g) is thereby obtained in the form of a white powder, m.p. 240° C. 3-[(4-Piperidyl)-carbonyl]indole is prepared according to the technique described in Chem. Abstr., 64, 14161f.

EXAMPLE 17

Hydroxylamine hydrochloride (0.3 g) is added to a solution of 4-benzoyl-1-[2-(3,4-dihydro-2H-1-benzopyran-4-yl)ethyl]piperidine hydrochloride (0.63 g) and an N solution (3.3 cc) of sodium hydroxide in absolute ethanol (20 cc), and the mixture is stirred at +20° C. for 16 hours. The solvents are evaporated off under reduced pressure (5.2 kPa) and the residue is taken up in water (25 cc) which is extracted with dichloromethane (3×25 cc). The combined organic phases are dried over magnesium sulphate and then concentrated to dryness under reduced pressure. The solid obtained is dissolved in boiling acetone (10 cc) and treated with oxalic acid (0.12 g) which is dissolved at the boil.

Z+E)-{1-[2-(3,4-Dihydro-2H-1-benzopyran-4-yl)ethyl]-4-piperidyl}phenylmethanoxine acid oxalate (0.37 g) is thereby obtained in the form of a white solid, melting from 130° C.

EXAMPLE 18

Triethylamine (1.03 cc) is added to a solution, cooled to between 0° to 5° C., of 1-[2-(3,4-dihydro-2H-1-benzopyran-4-yl)ethyl]piperazine (1.64 g) in dichloromethane (25 cc), and benzenesulphonic acid chloride (0.85 cc) is then introduced dropwise.

After 2 hours at 20° C., the mixture is diluted with distilled water (10 cc) and an identical quantity of 1N sodium hydroxide solution is added, and the mixture is then extracted twice with dichloromethane (10 cc). The organic phase is dried over magnesium sulphate and then concentrated to dryness under reduced pressure (5.2 kPa).

The residue obtained is chromatographed on a column 3 cm in diameter containing 60 g of silica gel, eluting with a dichloromethane/acetone mixture (70:30 by volume) and collecting 30-cc fractions. The fractions between 90 and 210 cc are concentrated to dryness under reduced pressure (5.2 kPa).

The oil obtained is taken up with ethanol (20 cc) and a 5N solution (3 cc) of hydrochloric acid in isopropanol is added, the mixture is concentrated to dryness and the product is recrystallized in 2-butanone (40 cc). 1-[2-(3,4-Dihydro-2H-1-benzopyran-4-yl)ethyl]-4-(phenylsulphonyl)piperazine hydrochloride (1.45 g) is thereby obtained in the form of a white solid, m.p. 164° C.

1-[2-(3,4-Dihydro-2H-1-benzopyran-4-yl) ethyl]piperazine may be prepared in the following manner;

The procedure is as in Example 1, starting with 4-(2-bromoethyl)-3,4-dihydro-2H-benzopyran (9.7 g), piperazine (10.4 g) and then potassium iodide (13.4 g) in 2-butanone (300 cc) but without the addition of potassium carbonate. The oil obtained is chromatographed on a column 4.4 cm in diameter containing silica gel (100 g), using a dichloromethane/ethanol/diethylamine mixture (80:18:2 by volume) as eluent. The fractions between 200 and 500 cc are concentrated to dryness.

1-[2-(3,4-Dihydro-2H-1-benzopyran-4-yl) ethyl]piperazine (7.1 g) is thereby obtained in the form of a oil, which is used without further treatment for the next step.

EXAMPLE 19

1-[2-(3,4-Dihydro-2H-1-benzopyran-4-yl) ethyl]piperazine (2.85 g), N-(2,6-dimethylphenyl)-3-chloropropionamide (2 g), dry potassium carbonate (1.23 g) and potassium iodide (1.48 g) in 2-butanone (70 cc) are heated to reflux for 12 hours.

The reaction mixture is filtered through sintered glass and the solvent is then evaporated off under reduced pressure (5.2 kPa). The oil obtained in taken up with 1N sodium hydroxide solution (15 cc) and then extracted twice with dichloromethane (150 cc). The organic phase is then washed with water and thereafter dried over magnesium sulphate.

After evaporation, an oil is obtained, which is purified by chromatography on a column 4.4 cm in diameter containing silica gel (100 g), eluting with a dichloromethane/isopropanol mixture (80:20 by volume) and collecting 50-cc fractions. The fractions between 1.3 and 2 liters are concentrated to dryness.

After recrystallization in isopropyl acetate, {1-[2-(3,4-dihydro-2H-1-benzopyran-4-yl)ethyl]-4-piperazinyl}-N-(2,6-dimethylphenyl)propanamide (1 g) is obtained in the form of a white solid, m.p. 130° C.

N-(2,6-Dimethylphenyl)-3-chloropropanamide may be prepared according to the method described in Beil, 12 III, 2464.

EXAMPLE 20

The procedure is as in Example 19, but starting with 1-[2-(3,4-dihydro-2H-1-benzopyran-4-yl)ethyl]-piperazine (2 g), N-(2,6-dimethylphenyl)chloroacetamide (1.6 g), dry potassium carbonate (1.12 g) and potassium iodide (1.34 g) in 2-butanone (80 cc).

After 2 hours 30 minutes under reflux, a residue is obtained, which is chromatographed on a column 4.4 cm in diameter containing silica gel (100 g), using an ethyl acetate/ethanol mixture (90:10 by volume) as eluent and collecting 25-cc fractions. The fractions between 475 and 1000 cc are concentrated to dryness under reduced pressure (5.2 kPa).

The oil obtained is taken up with ethanol (30 cc) and a 5.5N solution (1.3 cc) of hydrochloric acid in isopropanol is added.

After crystallization, {1-[2-(3,4-dihydro-2H-1-benzopyran -4-yl)ethyl]-4-piperazinyl}-N-(2,6-dimethylphenyl) acetamide hydrochloride (1 g) is obtained in the form of a white solid, m.p. approximately 230° C.

N-(2,6-Dimethylphenyl)chloroacetamide may be prepared according to the method described in Beil., 12 III, 2464.

EXAMPLE 21

The procedure is as in Example 4, but starting with 4-(2-bromoethyl)-3,4-dihydro-2H-benzopyran (1.9 g), N-(4-piperidyl)-4-fluorobenzamide hydrochloride (2 g), dry potassium carbonate (2.15 g) and potassium iodide (0.95 g) in 2-butanone (60 cc). The yellow oil obtained is purified by chromatography on a column 4 cm in diameter containing a silica gel (110 g), eluting with a toluene/diethylamine/ethanol mixture (60:20:20 by volume) (300 cc) and collecting 30-cc fractions. The fractions between 330 and 900 cc are concentrated to dryness. The yellow crystals obtained are dissolved in acetone (25 cc) and treated with a 3.4N solution (3 cc) of hydrochloric acid in isopropanol. The precipitate formed is filtered off on sintered glass and then recrystallized in an ethanol/acetone mixture (20:60 by volume) (80 cc). After the addition of ethyl ether (10 cc), N-{1-[2-(3,4-dihydro-2H-1-benzopyran-4-yl)ethyl]-4-piperidyl}-4-fluorobenzamide hydrochloride (2.05 g) is obtained in the form of a crystalline white solid, m.p. 240° C.

N-(4-Piperidyl)-4-fluorobenzamide hydrochloride may be prepared in the following manner:

N-(1-Benzyl-4-piperidyl)-4-fluorobenzamide hydrochloride (2.70 g) in 95% strength ethanol (50 cc) are hydrogenated at 60° C. at atmospheric pressure in the presence of palladium hydroxide (0.6 g). After filtration through kiselguhr and concentration to dryness under reduced pressure (5.2 kPa), white crystals are obtained, which are used without further treatment in the next step.

N-(1-Benzyl-4-piperidyl)-4-fluorobenzamide hydrochloride may be prepared in the following manner:

4-Aminobenzylpiperidine (2 g), dissolved in dichloromethane (20 cc), is stirred for 2 hours at 0° C. with 4-fluorobenzoic acid chloride (1.30 cc) in the presence of triethylamine (1.5 cc). After 18 hours at room temperature, the reaction mixture is washed with 30% strength ammonia solution and then with water until the pH is neutral. The organic phase is then dried over magnesium sulphate and thereafter concentrated under reduced pressure (5.2 kPa).

The yellow crystals obtained are purified by chromatography on a column 4 cm in diameter containing silica gel (70 g), eluting with a toluene/diethylamine/ethanol mixture (80:10:10 by volume) (480 cc) and collecting 30 cc fractions. The fractions between 120 cc and 4800 cc are concentrated to dryness.

The white crystals obtained are taken up with dichloromethane (20 cc) and a 3.5N solution (3 cc) of hydrochloric acid in isopropanol. N-(1-Benzyl-4-piperidyl)-4-fluorobenzamide hydrochloride (2.70 g), m.p. 236° C., is thereby obtained.

EXAMPLE 22

The procedure is as in Example 4, but starting with 4-(2-bromoethyl)-3,4-dihydro-2H-benzopyran (0.70 g), N-phenyl-N-(4-piperidyl)methanesulphonamide hydrochloride (0.75 g), dry potassium carbonate (0.75 g) and potassium iodide (0.35 g) in 2-butanone (45 cc). The yellow oil obtained is purified by chromatography on a column 4 cm in diameter containing silica gel (60 g), eluting with a dichloromethane/ethanol mixture (95:5 by volume) (660 cc) and collecting 30-cc fractions. The fractions between 120 cc and 660 cc are concentrated to dryness. The oil obtained is taken up with ethanol (10 cc) and fumaric acid (0.35 g), dissolved in ethanol (10 cc) is added. The mixture is concentrated to dryness and the crystals are washed with acetone and recrystallized in isopropanol (20 cc).

{1-[2-(3,4-Dihydro-2H-1-benzopyran-4-yl)ethyl]-4-piperidyl}-N-phenylmethanesulphonamide acid fumarate (0.310 g) is thereby obtained in the form of a white solid, m.p. 186° C.

N-Phenyl-N-(4-piperidyl)methanesulphonamide hydrochloride may be prepared in the following manner:

N-(1-Benzyl-4-piperidyl)-N-phenylmethanesulphonamide hydrochloride (1.16 g) in 95% strength ethanol (50 cc) is hydrogenated at 60° C. at atmospheric pressure in the presence of palladium hydroxide (0.3 g).

After filtration through kieselguhr and concentration to dryness under reduced pressure (5.2 kPa), white crystals (0.758 g) are obtained, which are used without further treatment in the next step.

N-(1-Benzyl-4-piperidyl)-N-phenylmethanesulphonamide may be prepared in the following manner:

1-Benzyl-4-anilinopiperidine (5.8 g), dissolved in dichloromethane (40 cc), is stirred under argon for 7 hours at 0° C. with methanesulphonic acid chloride (2 cc) and in the presence of triethylamine (3 cc). After treatment as described in Example 21, an oil is isolated, which is chromatographed by HPLC (on a Waters Prep. 500 with a Prep. PAK column 5 cm in diameter and 30 cm long containing 55–105 $\mu$ silica), using a dichloromethane/isopropyl acetate mixture (5:1 by volume) as eluent and collecting the fractions between 1500 cc and 2350 cc.

N-(1-Benzyl-4-piperidyl)-N-phenylmethanesulphonamide (1.05 g) is thereby obtained in the form of a white solid, m.p. 125° C.

1-Benzyl-4-anilinopiperidine has been prepared according to the method described in Dutch Patent Application 65 06 574.

EXAMPLE 23

The procedure is as an Example 4, but starting with 4-(2-bromoethyl)-3,4-dihdro-2H-benzopyran (1.6 g), N-phenyl-N-(4-piperidyl)benzenesulphonamide hydrochloride (2.34 g), dry potassium carbonate (1.8 g) and potassium iodide (0.8 g) in 2-butanone (50 cc).

The oil obtained is taken up in the minimum amount of ethanol and benzensulphonic acid (1 g), dissolved in ethanol, is added. The white precipitate formed is filtered off on sintered glass and then recrystallized in an ethanol/methanol mixture (50:50 by volume) (80 cc).

N-{1-[2-(3,4-Dihydro-2H-1-benzopyran-4-yl)ethyl]-4-piperidyl}-N-phenylbenzenesulphonamide benzenesulphonate (2.45 g) is thereby obtained in the form of a white solid, m.p. 150° C.

N-Phenyl-N-(4-piperidyl)benzenesulphonamide hydrochloride may be prepared as described in Example 22 for N-phenyl-N-(4-piperidyl)methanesulphonamide.

The present invention also relates to pharmaceutical compositions consisting of a product of general formula (I), in free form or in the form of an addition salt with a pharmaceutically acceptable acid, in the pure state or in the form of a combination with any other pharmaceutically compatible product, which can be inert or physiologically active. The compositions according to the invention may be used orally or parenterally.

As solid compositions for oral administration, tablets, pills, powders or granules may be used. In these compositions, the active product according to the invention (optionally combined with another pharmaceutically compatible product) is mixed with one or more inert adjuvants or diluents such as sucrose, lactose or starch. These compositions can also comprise substances other than diluents, for example a lubricant such as magnesium stearate.

As liquid compositions for oral administration, emulsions of a pharmaceutically acceptable nature, solutions, suspensions, syrups or elixirs containing inert diluents such as water or liquid paraffin may be used. These compositions can also comprise substances other than diluents, e.g. wetting products, sweeteners or flavourings.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. be asptic filtration by incorporating sterilizing agents int he composition, by irradiation or by heating. They may also be prepared in the form of sterile solid compositions which can be dissolved at the time of use in a sterile injectable medium.

The pharmaceutical compositions according to the invention, which reduce heart rhythm disorders due to re-entry phenomena, treated or untreated, are especially useful in human therapy in treatments following myocardial infarction, as well as in chronic anginal states and ischaemic type cardiopathies.

Generally speaking, the doctor will determine the dosage he considers most appropriate in accordance with the age, weight and other factors characteristic of the subject to be treated.

In general, the doses are between 0.25 and 1.5 g per day of active product administered orally or intravenously for an adult.

The examples which follow, given without implied limitation, illustrate a composition according to the invention.

EXAMPLE A

Tablets having the following composition are prepared:

| | |
|---|---|
| {1-[2-(3,4-dihydro-2H-1-benzopyran-4-yl)ethyl]-4-piperidyl}acetanilide acid oxalate | 161 mg |
| lactose | 50 mg |
| excipient q.s. | 250 mg |

EXAMPLE B

Tablets having the following composition are prepared:

| | |
|---|---|
| 4-benzoyl-1-[2-(3,4-dihydro-2H-1-benzopyran-4-yl)ethyl]piperidine hydrochloride | 165.6 mg |
| lactose | 50 mg |
| excipient q.s. | 250 mg |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A benzopyran compound having the formula:

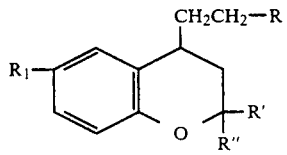

wherein
R₁ represents a hydrogen or halogen atom or a hydroxy, alkyloxy, nitro, amino, alkylsulphonamido or acylamino radical, R represents (1) a radical of formula:

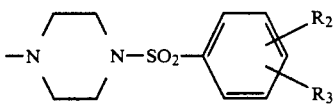

wherein R₂ and R₃, which may be identical or different, represent hydrogen or halogen atoms or hydroxy, alkyl, alkyloxy, amino, alkylsulphonamido or nitro radicals, or alternatively (2) a radical of formula:

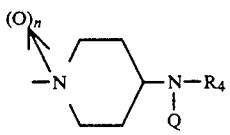

wherein n equals 0 or 1, R₄ is a hydrogen atom, an alkyl radical or a radical of structure:

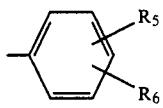

wherein R₅ and R₆ are hydrogen or halogen atoms or an alkyloxy radical, and Q represents an acyl or alkylsulphonyl radical or a radical of structure:

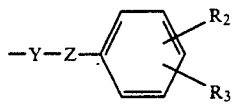

wherein R₂ and R₃ are defined as above, Y represents a carbonyl or sulphonyl radical and Z represents a single bond or a methylene or imino radical, or alternatively (3) a radical of formula:

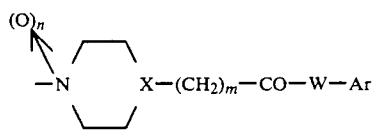

wherein n equals 0 or 1, m equals 0 to 2, X is a carbon atom or X can be a nitrogen atom if n=0, W represents a single bond or an imino radical and Ar represents a pyridyl, indolyl, quinolyl or 2-alkylquinolyl radical or a phenyl radical optionally substituted with radicals R₂ and R₃ as defined above, provided that m is other than 0 when X is a nitrogen atom, or alternatively (4) a radical of formula: (VI)

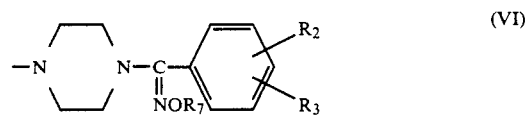

wherein R₂ and R₃ are defined as above and R₇ denotes a hydrogen atom or an alkyl radical, or alternatively (5) a radical of formula:

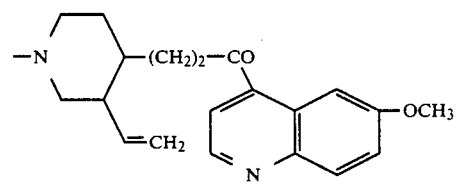

and R' and R'', which are identical, represent hydrogen atoms or alkyl radicals,
on the understanding that the alkyl and acyl radicals and portion mentioned above contain 1 to 4 carbon atoms in a straight or branched chain, in its isomeric forms and the mixtures thereof, as well as its pharmaceutically acceptable addition salts with acids.

2. A benzopyran compound according to claim 1, wherein R₁, R' and R'' are hydrogen atoms, and R represents a radical as defined at (1) for which $R_2$ and $R_3$ are hydrogen atoms, or R represents a radial as defined at (2) for which n equals 0, $R_4$ is a hydrogen atom, an alkyl radical or a radical of structure:

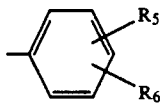
(IVa)

in which $R_5$ and $R_6$ are hydrogen or halogen atoms or alkyloxy radicals and Q represents an acetyl or methylsulphonyl radical or a radical of formula:

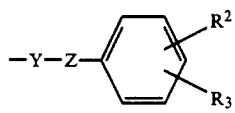
(IVb)

wherein Y is a carbonyl or sulphonyl radical and Z is a bond or a methylene or imino radical, and $R_2$ and $R_3$ are hydrogen or halogen atoms or alkyl or methylsulphonamido radicals, or R represents a radical as defined at (3) for which n equals 0, m equals 0 to 2, W is a bond or an imino radical, Ar is pyridyl, indolyl or phenyl optionally substituted with a halogen atom or alkyl or alkyloxy radicals and X is a carbon or nitrogen atom, or R represents a radical as defined at (4) for which $R_7$ represents a hydrogen atom.

3. N-{1-[2-(3,4-Dihydro-2H-1-benzopyran-4-yl)ethyl]-4-piperidyl}acetanilide or a pharmaceutically acceptable salt thereof.

4. 1-[2-(3,4-Dihydro-2H-1-benzopyran-4-yl)ethyl]-4-or a pharmaceutically acceptable salt thereof.

5. N-{1-[2-(3,4-Dihydro-2H-1-benzopyran-4-yl)ethyl]-4-piperidyl}-N-phenyl-4-fluorobenzamide or a pharmaceutically acceptable salt thereof.

6. 4-Benzoyl-1-[2-(3,4-dihydro-2H-1-benzopyran-4-yl)ethyl]piperidine or a pharmaceutically acceptable salt thereof.

7. {1-[2-(3,4-Dihydro-2H-1-benzopyran-4-yl)ethyl]-4-piperidyl}phenylmethanoxime or a pharmaceutically acceptable salt thereof.

8. A pharmaceutical composition, which comprises an effective amount benzopyran compound according to claim 1, in the pure state or in the form of a combination with one or more compatible and pharmaceutically acceptable adjuvants or diluents.

* * * * *